United States Patent [19]

Duggan et al.

[11] 4,272,440
[45] Jun. 9, 1981

[54] INTERMEDIATES FOR PREPARING HYDROXYPHENYLPYRIDAZINONES

[75] Inventors: Angelina J. Duggan, Lawrenceville, N.J.; Robert L. Webb, West Chester, Pa.

[73] Assignee: SmithKline Corporation, Philadelphia, Pa.

[21] Appl. No.: 8,732

[22] Filed: Feb. 2, 1979

Related U.S. Application Data

[62] Division of Ser. No. 880,928, Feb. 24, 1978, abandoned.

[51] Int. Cl.³ .......................................... C07D 307/58
[52] U.S. Cl. ................................. 260/343.6; 549/239
[58] Field of Search ...................................... 260/343.6

[56] References Cited

U.S. PATENT DOCUMENTS 3,193,552  7/1965  Dury et al. ............................ 260/250
4,053,601  10/1977  Coates et al. ........................ 424/250

Primary Examiner—Henry R. Jiles
Assistant Examiner—Bernard Dentz
Attorney, Agent, or Firm—William H. Edgerton; Richard D. Foggio; Alan D. Lourie

[57] ABSTRACT 5-(5'-Halo-2'-methoxyphenyl)-3,4-dihalo-2(5H)-furanones are prepared by a Friedel-Crafts reaction using a p-haloanisole and a mucohalic acid in the presence of aluminum chloride. They are used as chemical intermediates for preparing hydroxyphenylpyridazinones.

2 Claims, No Drawings

INTERMEDIATES FOR PREPARING HYDROXYPHENYLPYRIDAZINONES

This is a divisional of application Ser. No. 880,928 filed Feb. 24, 1978 now abandoned.

This invention relates to a new method of preparing 6-(2'-hydroxyphenyl)-3-pyridazinones which are of use as intermediates for preparing antihypertensive agents or reactive dyes (U.S. Pat. Nos. 4,053,601 and 3,193,552). The method of this invention is characterized by the reaction under Friedel-Crafts conditions of a mucohalic acid with a p-haloanisole followed by formation of the pyridazinone ring using hydrazine then dehalogenation.

PRIOR ART STATEMENT

U.S. Pat. No. 4,053,601 (see scheme 6 thereof) discloses the condensation of mucohalic acids with a phenol whose para-position is blocked by a t-butyl group followed by ring formation, ring dehalogenation and removal of the t-butyl group. This reference does not disclose the use of a p-haloanisole as starting material or other distinguishing aspects of the present invention which will be discussed at greater length hereafter. U.S. Pat. No. 3,193,552 discloses the condensation of mucohalic acids with various aryl compounds but none with the critical p-haloanisole structure. Other art such as V. Zikan et al., Coll. Czechoslov. Chem. Comm. 32, 2374 (1967), V. Ettel et al., Chem. Listy 16, 634 (1952) and V. Ettel et al., Chem. Listy 46, 232 (1952) disclose the condensation, in the para-position, of various halo or alkoxybenzenes with mucohalic acids but none with a p-haloanisole or with conditions for the preparation of ortho derivatives.

The overall process of this invention is illustrated by the following reaction sequence in its preferred form:

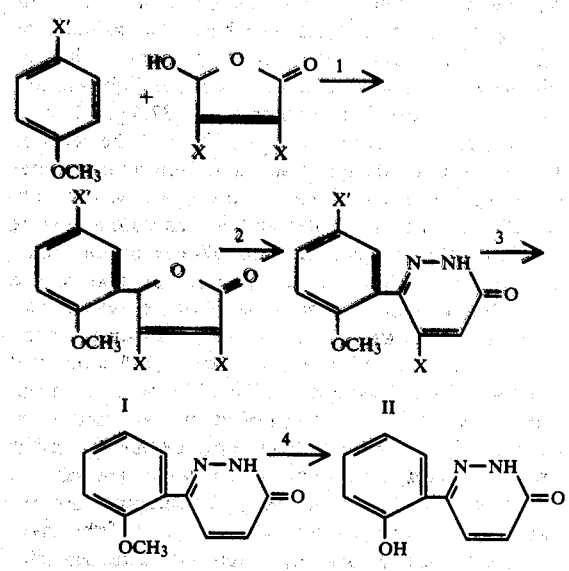

in which X and X' are bromo or preferably chloro.

It will be appreciated by those skilled in the art that the reaction of step 1 to yield the γ-lactone (I) involves a Friedel-Crafts acylation by the aldehyde carbon of the mucohalic acid which has been shown to exist in the cyclic form:

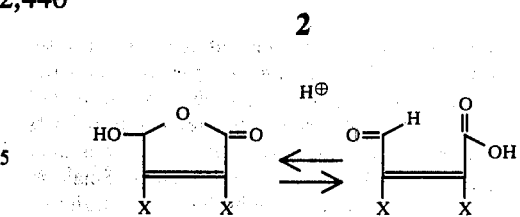

The reaction is more sluggish than the usual Friedel-Crafts acylation involving acid chlorides and also proceeds poorly with a p-halophenol or a higher alkoxy p-halobenzene.

The prior art teaches that alkoxy groups such as methoxy are predominantly para directing in this reaction with catalysts that may be chosen over a wide range, either the Lewis acid type such as aluminum chloride, boron trifluoride, zinc chloride and the like or dehydration catalysts such as concentrated sulfuric acid, glacial acetic acid, conc. hydrobromic acid, polyphosphoric acid and the like.

We have found that, using anisoles, good yields of ortho substituted product are obtained (a) if the paraposition of the anisole is blocked with a chloro or bromo substituent, (b) if aluminum chloride is used as catalyst and (c) if a small, nonbulky ether group is present especially the methoxy group of anisole. Other catalysts such as zinc chloride, polyphosphoric acid or zinc chloride-polyphosphoric acid give little or no condensation. If a bulky ether is present, such as a "β-blocking" side chain for example 3-t-butylamino-2-hydroxypropoxy, the condensation is equally unsuccessful.

If desired, the methoxy group can be split at this stage such as by using an excess of aluminum chloride at dichloroethane reflux but it is usually preferred to remove the methyl group later in the sequence for the best yields.

The Friedel-Crafts reaction of step one is carried out by reacting approximately equimolar quantities of p-haloanisole, aluminum chloride and mucohalic acid in a solvent inert under the reaction conditions in which the reactants are soluble. The solvent is most conveniently a common halogenated hydrocarbon such as carbon tetrachloride, chloroform, methylene chloride, dichloroethane, tetrachloroethylene and the like. The reaction is run at a temperature chosen from about 0° to the reflux temperature of the reaction mixture. Most conveniently the reactants are mixed at cool temperatures such as from 5°–10°, then allowed to react at ambient temperature until the reaction is substantially complete, often 1–3 days, followed by a brief period of reflux.

After working up by standard isolation methods, yields of the desired 5-(5'-halo-2-methoxyphenyl)-3,4-dihalo-2(5H)-furanone range from 60–80%.

The crotonolactone product (I) is then reacted with from about 1 to 2 molar equivalents of hydrazine preferably as the hydrate (step 2). Larger amounts of hydrazine yield substantial quantities of 5-hydrazino-6-(2'-methoxy-5'-halophenyl)-3-pyridazinone due to the replacement of the 5-chloro atom by the excess hydrazine. The presence of an excess of base during the reaction is suggested such as a common organic amine as a lower alkylamine for example, n-propylamine, n-butylamine, diethylamine, dimethylamine etc. The solvent may be any inert organic solvent in which the products are soluble such as water, methanol, ethanol or, less desirably tetrahydrofuran, dimethylformamide, formamide, or mixtures thereof.

Satisfactory yields of the desired pyridazinone are obtained by reacting the crotonolactone with a slight excess of hydrazine as described at temperatures selected from about 0° to ambient temperature until the reaction is substantially complete usually from 1-8 hours. Higher temperatures and shorter reaction times gave no better yields. More vigorous conditions give substitution at the 5-halo group. The desired 5-halo-6-(2'-methoxy or hydroxy-5'-halophenyl)-3-pyridazinone is isolated from the reaction mixture by standard chemical isolation methods in yields of 75-95%. For convenience the lower alkyl groups in the organic amines are limited to 1-6 carbons, straight or branched.

The next reaction (step 3) involves the removal of the halo substituents from both the phenyl and pyridazinone rings. Once again such a dehalogenation may be optionally run on the 2'-hydroxy or the 2'-methoxyphenyl-3-pyridazinone.

The preferred catalytic hydrogenation is carried out at low pressure (20-60 p.s.i. hydrogen) and any palladium catalyst known to the art may be used, for example, palladium supported on carbon, alumina, barium sulfate or calcium carbonate. The percentage of palladium is most conveniently from 2.5 to 10%, preferably 5-10%, of the support medium. Other similar palladium hydrogenation catalysts can be substituted but with little advantage.

Dehalogenation using palladium-on-charcoal is known to the art to require about 20% of the catalyst relative to the substrate being reduced. We on the other hand have found that, even when the substrate is crude, amounts in the range of 1-3% of palladium-on-charcoal based on the halophenol starting material give excellent yields.

The solvent may be any inert protic solvent known to be used in the hydrogenation art in which the reactants are soluble. Most useful are the lower alcohols such as methanol, ethanol or isopropanol and especially aqueous mixtures thereof.

The presence of at least 2 mole equivalents of a base which is preferably an inorganic base such as an alkali metal hydroxide, carbonate or bicarbonate or an alkaline earth metal carbonate and is most preferably sodium or potassium hydroxide suppresses hydrogenation of the keto group and leads to the high yields realized. Preferably from 2.25-3 mole equivalents of base are used but more than 3 mole equivalents may also be used. Alternatively other bases may be used including organic bases such as trimethylamine, triethylamine, pyridine and the like. Of course the source of base may also be the supporting medium for the palladium catalyst such as strontium, calcium or barium carbonate.

The hydrogenation is most conveniently run at from about room temperature up to about 60° for from ¼ to 6 hours. The reaction mixture is worked up by standard methods similar to those described in the working examples hereinafter. Yields of 85-95% of highly pure products are realized.

The optional final step of the sequence (step 4) comprises the splitting of the 2'-methoxy substituent if present. In fact this may be accomplished by any method known to the art for splitting methyl phenyl ethers such as the use of strong alkali, a Lewis acid such as aluminum chloride or strong acid such as a hydrohalic acid. Preferably aluminum chloride or concentrated hydrobromic acid are used.

For example the product of step 3 is heated at reflux for from ½-48 hours with an excess of aluminum chloride in an inert organic solvent in which the reactants are soluble such as a halogenated hydrocarbon for example dichloroethane or methylene chloride. Alternatively the 2'-methoxy compound is heated with an excess of 48% hydrobromic acid alone or in glacial acetic acid until the reaction is complete. Excellent yields of the desired 6-(2'-hydroxyphenyl)-3-pyridazinone are obtained by either method.

As stated above the splitting of the 3-methoxy group may be carried out optionally during step 1 by using an excess of aluminum chloride, or prior to steps 2 or 3 by the method outlined above.

The intermediates designated as I and II in the reaction sequence above are, to the best of our knowledge, new compounds and are a part of this invention.

There are a number of variations of this invention which will be recognized as possible by those skilled in the art. For example the blocking para substituent in the anisole starting material may be any substituent removed by hydrogenation such as iodo, bromo or chloro. For economic reasons the chloro is preferred. The two halo substituents on the mucohalic acid may be bromo or chloro but for economic reasons again chloro is preferred. It is also obvious that the two halo atoms on the mucohalic acid may differ from the anisole blocking substituent. Also the methoxy substituent may be altered to an ethoxy group but as stated above larger groups tend to give lower yields in the Friedel-Crafts reaction (step 1).

The following examples are designed to illustrate the practice of this invention. Melting points are in degrees Centigrade.

EXAMPLE 1

5-(5'-Chloro-2'-methoxyphenyl)-3,4-dichloro-2(5H)furanone

A solution of 28.5 g of p-chloroanisole (0.2 mol) in 100 ml of dry methylene dichloride was cooled with stirring in an ice bath to ≈5°. Solid aluminum chloride (26.6 g, 0.2 mol) was added at such a rate to maintain the temperature below +10°. As the aluminum chloride dissolved, the colorless solution became light tan and more viscous. Solid mucochloric acid (37.4 g, 0.22 mol) was added via a Gooch tube (≈10°) and the reaction was allowed to warm and stir at ambient temperatures for 2 days. After 2 days the green solution was brought to reflux for 1 hour, cooled and poured onto a mixture of 250 ml of methylene chloride, 200 g of ice and 10 ml of conc. hydrochloric acid. The aqueous mixture was extracted with an additional 100 ml of methylene chloride and the combined extracts were washed successively with water (100 ml) and brine (100 ml), dried over anhydrous magnesium sulfate, filtered and concentrated to yield 48.0 g of crude product. The crude product was taken up in methylene chloride (150 ml), cooled and the unreacted mucochloric acid which precipitated was separated by filtration (6 g). The methylene chloride was concentrated to yield 42 g (72%) of the crude lactone which contains some unreacted p-chloroanisole. The lactone was recrystallized from anhydrous ethanol to give 35.1 g (60%) of colorless crystals, m.p. 87°-89°.

$C_{11}H_7Cl_3O_3$ (293.536). Calculated: C, 45.01; H, 2.40; Cl, 36.23. Found: C, 45.34; H, 2.44; Cl, 36.45.

Spectra (u.v., n.m.r. and mass spec) were all consistant with the expected structure.

EXAMPLE 2

5-(5'-Bromo-2'-methoxyphenyl)-3,4-dichloro-2(5H)furanone

A solution of p-bromoanisole (18.7 g, 0.1 mol) in 100 ml of dry methylene chloride was reacted similarly to p-chloroanisole in Example 1 with 13.5 g (0.1 mol) aluminum chloride and 18.77 (0.11 mol) of mucochloric acid. The reaction was worked up similarly and 6 g of unreacted mucochloric acid was isolated. Crystallization of the desired lactone from the crude reaction mixture yielded 10 g (38%), colorless crystals, m.p. 96°.

$C_{11}H_7BrCl_2O_3$ (337.987). Calculated: C, 39.09; H, 2.09; Br, 23.64; Cl, 35.91. Found: C, 39.16; H, 2.26; Br, 24.00; Cl, 36.00.

Substituting an equivalent amount of mucobromic acid in the reaction of Example 1 gives 6-(5'-Bromo-2'-methoxyphenyl)-3,4-dibromo-2(5H)furanone.

EXAMPLE 3

5-Chloro-6-(2'-methoxy-5'-chlorophenyl)-3-pyridazinone

A. A sample of 14.6 g (0.05 mol) of the lactone from Example 1 was stirred in 150 ml of methanol. The colorless suspension was cooled in an ice bath and 2.75 g (0.055 mol) of hydrazine hydrate was added, heat followed by 3.0 g (0.05 mol) of n-propylamine. The reactants were stirred in an ice bath for ½ hour and then warmed to ambient temperatures. The colorless suspension became a clear yellow solution and gradually there was observed the precipitation of a white solid. After 5 hours the methanol was removed in vacuo and the crude product was partitioned between methylene chloride and water, the methylene chloride was dried, filtered, and concentrated to yield 12 g (90%) of the desired pyridazinone.

B. A sample of 4.4 g (0.015 mol) of the lactone was stirred rapidly in 45 ml of water. The reactants were cooled in an ice bath and the hydrazine hydrate (1.5 g, 0.03 mol) and diethylamine (1.1 g, 0.015 mol) were added. The colorless slurry was warmed to ambient temperatures after 15 minutes and allowed to stir for 8 hours. The reaction was partitioned between methylene chloride and water; the methylene chloride was dried, filtered and concentrated to yield 3.2 g (82%) of the crude product which was recrystallized from ethanol to give 3.0 g (75%) of the purified pyridazinone, m.p. 226°.

$C_{11}H_8O_2Cl_2N_2$ (271.105). Calculated: C, 48.72; H, 2.97; N, 10.33; Cl, 26.15. Found: C, 48.79; H, 2.97; N, 10.14; Cl, 25.85.

We have found that there tends to be less reaction at the 5-halo site in water than in alcohol hence more of the hydrazine reactant can be used in an aqueous solvent.

EXAMPLE 4

6-(2'-Methoxybenzene)-3-pyridazinone

Into a 500 ml pressure bottle was placed 4.08 g (0.015 mol) of the dichloropyridazinone of Example 3, 4.5 g (0.033 mol) of triethylamine and 0.5 g of 5% palladium-on-charcoal. The bottle was placed in a Parr apparatus and hydrogenated at 55 p.s.i. at 40° for 5 hours. The reaction was filtered through a filter aid (Celite). The filtrate was concentrated in vacuo. The residue was partitioned between methylene chloride and water; the organic layer was dried, filtered and concentrated to yield 3.2 g of the dehalogenated pyridazinone, m.p. 166°.

$C_{11}H_{10}O_2N_2$ (202.215). Calculated: C, 65.34; H, 4.98; N, 13.85. Found: C, 65.29; H, 5.20; N, 14.07.

Similarly equimolar quantities of sodium hydroxide, potassium hydroxide, potassium acetate or potassium bicarbonate may be substituted for the organic amine in the above procedure.

EXAMPLE 5

6-(2'-Hydroxyphenyl)-3-pyridazinone

A. A 2.2 g (0.0108 m) sample of the pyridazinone from Example 4 was dissolved in 50 ml of 1,2-dichloroethane. Solid aluminum chloride (4.32 g, 0.0324 mol) was added. The mixture was stirred well and brought to reflux. The red solution was heated at reflux for 30 hours and during the course of the reaction a gummy solid precipitated (aluminum complexed phenol). The reaction was poured onto a mixture of 100 g of ice and 2 ml of conc. hydrochloric acid and stirred until all of the gum was dissolved and a white precipitate had formed. The precipitate was filtered and washed with water until the washings were neutral, then successively with ethyl ether and methylene chloride and dried in vacuo over phosphorus pentoxide to obtain 2.0 g, a quantitative yield, of the demethylated pyridazinone, m.p. 286°–290°.

B. The pyridazinone (0.202 g, 0.001 mol) was refluxed in a mixture of 2 ml of 48% hydrobromic acid and 4 ml of glacial acetic acid. After 20 hours the yellow solution was concentrated and the solid residue was filtered and washed with water, ethyl ether, methylene chloride and dried in vacuo to yield 180 mg (96%) of the demethylated pyridazinone, m.p. 288°–290°.

C. Into a 500 ml pressure bottle was placed 2.0 g (0.007 mol) of 6-(5'-chloro-2'-hydroxyphenyl)-5-chloro-3-pyridazinone (produced from aluminum chloride/methylene chloride on the 2'-methoxy congener), 3.1 g (0.03 ml) of triethylamine and 0.5 g palladium-on-charcoal. The bottle was placed in a Parr apparatus and hydrogenated under 57 p.s.i. at 50° for 10 hours. The reaction was filtered through a fine glass filter and the solids were washed 4 times with 25 ml of 0.5 N sodium hydroxide. The filtrate was cooled, acidified, and filtered to give 0.7 g (48%) of the pyridazinone, m.p. 286°–288°.

EXAMPLE 6

5-Chloro-6-(2'-hydroxy-5'-chlorophenyl-3-pyridazinone

The pyridazinone (1.35 g, 0.005 m) was added to a solution of aluminum chloride (2.0 g, 0.015 m) in 25 ml of 1,2-dichloroethane. The resultant green solution was brought to reflux and, as the demethylation proceeded, a precipitation of a fine solid formed. After 24 hours, the green slurry was poured onto ice-water. The solids were collected by filtration and washed with water until the washings were neutral, and with two 25 ml portions of ether and once with methylene chloride to give 1.14 g (85%) of the demethylated pyridazinone as a yellow solid, m.p. 243°–244°. The pyridazinone could be crystallized from methanol to yield 1.07 g (83%) of colorless crystals, m.p. 246°–247°.

EXAMPLE 7

5-Hydrazino-6-(2'-methoxy-5'-chlorophenyl)-3-pyridazinone

A mixture of 1.5 g (0.005 mol) of 5-chloro-6-(2'-methoxy-5'-chlorophenyl)-3-pyridazinone chloroanisole-6-pyridazinone and 25 ml of hydrazine hydrate was heated at reflux for 4 hours. The solution was cooled and the white solid which formed was separated, washed with water (30 ml) and dried at 40° in a vacuum oven overnight to give 1.2 g (81%) of a colorless solid product, m.p. 285°–290°.

$C_{11}H_{11}ClN_4O_2$. Calculated: C, 49.54; H, 4.16; N, 21.01. Found: C, 49.54; H, 4.24; N, 21.41.

What is claimed is:

1. A compound of the formula:

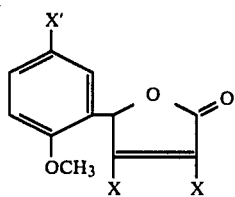

in which X' is bromo or chloro and both variables denoted by X are either bromo or chloro.

2. The compound of claim 1 in which X' and X are chloro.